(12) United States Patent
Meyerson

(10) Patent No.: US 6,996,477 B2
(45) Date of Patent: Feb. 7, 2006

(54) COMPUTATIONAL SUBTRACTION METHOD

(75) Inventor: Matthew L. Meyerson, Concord, MA (US)

(73) Assignee: Dana Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 09/839,186

(22) Filed: Apr. 19, 2001

(65) Prior Publication Data

US 2002/0015955 A1   Feb. 7, 2002

(51) Int. Cl.
G01N 33/48 (2006.01)
G01N 33/50 (2006.01)
G06F 19/00 (2006.01)

(52) U.S. Cl. ............... 702/20; 702/19; 707/1; 707/3; 707/104

(58) Field of Classification Search .......... 702/19, 702/20; 707/1–10, 104.1, 104
See application file for complete search history.

(56) References Cited

U.S. PATENT DOCUMENTS

| 5,966,711 A | 10/1999 | Adams ............... 707/104 |
| 5,966,712 A | 10/1999 | Sabatini et al. ....... 707/104 |
| 6,114,114 A | 9/2000 | Seilhammer et al. ..... 435/6 |
| 6,185,561 B1 | 2/2001 | Balaban et al. ........ 707/6 |
| 6,303,297 B1 * | 10/2001 | Lincoln et al. ........ 435/6 |

FOREIGN PATENT DOCUMENTS

WO   WO 01/54557 A2 *   8/2001

OTHER PUBLICATIONS

Relman et al. Nature Genetics, 30(2):131-133, Feb. 2002.*
Weber et el., Nature Genetics, 30(2):141-142, Feb. 2002, including supplementary information from web site.*
Cummings and Relman, Using DNA Microarrays to Study Host-Microbe Instructions, *Emerg. Infect. Dis* 6(5):513-525 (2000).
Lisitsyn, Representational difference analysis: finding the differences between genomes, *Trends Genetics* 11:303-307 (1995).
Maiwald et al, Whipple's Disease and *Tropheryma whippelii*: Secrets Slowly Revealed, *Clin Infect. Dis* 32(3):457-463 (2002).
Relman et al, The Agent of Bacillary Angiomatosis, *New England. J. Med.* 323:1573-1580 (1990).
Wan, et al, Cloning Differentially Expressed mRNAs, *Nature Biotechnology*, 14:1685-1691 (1996).
International Search Report PCT/US01/12736.
Zhang et al., "A Greedy Algorithm for Aligning DNA Sequences," Journal of Computational Biology 7 (1/2): 203-214(2001).
Balter, "Molecular Methods Fire Up the Hunt for Emerging Pathogens," Science 282: 21-23 (1998).
Fredericks et al., "Application of Polymerase Chain Reaction to the Diagnosis of Infectious Diseases," CID 29:475-488 (1999).

* cited by examiner

*Primary Examiner*—Marianne P. Allen
(74) *Attorney, Agent, or Firm*—Kathleen Williams; Mark J. FitzGerald; Palmer & Dodge, LLP

(57) ABSTRACT

The invention provides a method and system for performing computational subtraction to detect microbes within a host organism. In some aspects, the microbes are pathogens and the system is used to identify sequences belonging to these pathogens which can then be used in methods of diagnosis and treatment. Alternatively, the microbes can be symbiotic organisms, such as commensal or parasitic organisms. Preferably, candidate sequences identified as belonging to a microbe are used to isolate and clone additional sequences from the microbe.

36 Claims, 2 Drawing Sheets ated with pathogenesis. Therefore, in one aspect, the invention provides a method of using a computer system to identify a microbe inhabiting a host organism which comprises the steps of obtaining sequence information from a plurality of sequences from at least one host organism and searching a database of host organism genomic sequences to determine the presence or absence of the plurality of expressed sequences in the database. The absence of at least one of the sequences in the database indicates that the at least one sequence is a candidate microbe sequence. Individual sequences can be searched sequentially; however, preferably, sets of sequences are searched at a time.

COMPUTATIONAL SUBTRACTION METHOD

FIELD OF THE INVENTION

The invention relates to a method and system for detecting microbes harbored by a host organism. In particular, the invention relates to a method and system for detecting novel infectious disease organisms associated with the pathogenesis of human diseases.

BACKGROUND OF THE INVENTION

Humans and animals are in continuous contact with microorganisms. Generally, because of the effectiveness of host defense mechanisms these microorganisms do not cause disease. However, some microorganisms (e.g., opportunistic pathogens) can become infective in particular types of individuals, such as those who are immunocompromised. Still other microorganisms are extremely virulent upon contact. For example, microorganisms such as the Ebola virus are associated with close to 100% fatality rates.

Traditional methods of correlating disease symptoms with the presence of a microorganism rely on identifying through symptoms and/or through epidemiological studies, the likelihood that the disease is caused by an infectious agent and attempting to culture appropriate samples from the individual to isolate and identify the agent. This can be problematic where epidemiological evidence is unclear, particularly in the case of pathogens with long incubation periods (e.g., up to 10 years in the case of HIV and 20–30 years in the case of *Mycobacterium leprae*).

Even where epidemiological evidence suggests an infectious cause for a disease, the microorganisms responsible for these diseases can evade detection. For example, Whipple's disease, a debilitating disease associated with diarrhea and weight loss, was for many years described as "intestinal lipodystrophy" because no microorganism could be cultured from samples from patients with disease. However, the microbial origin of Whipple's was suggested by the dramatic response of patients to antibiotics and the presence of bacilli observed in electron micrographs of affected tissues. Still, the identification of the infectious organism as an actinomycetes awaited the advent of molecular techniques such as PCR. See, e.g., Maiwald et al., Clin. Infect. Dis. 32(3): 457–463 (2001). PCR amplification of conserved ribosomal sequences also led to the detection of another unculturable bacteria, the causative agent of bacillary angiomatosis which is associated with the proliferation of small blood vessels in the skin and visceral organs of patients with AIDS (see, Relman et al., New Engl. J. Med. 323: 1573–1580 (1990)). Another molecular technique, the DNA subtractive cloning method—representational difference analysis (Lisitsyn, Trends Genetics 11: 303–307 (1995)), enabled the discovery of the herpesvirus causing Kaposi's sarcoma (Chang et al., Science 265: 1865–1869 (1994)).

A high throughput approach to identifying infectious organisms has been described by Cummings and Relman, Emerg. Infect. Dis. 6(5): 513–25 (2000). Cummings and Relman report using a DNA microarray comprising sequences from known pathogens to detect the presence pathogens in patient samples. However, the method will only be able to detect pathogens for which at least some sequence information is known.

SUMMARY OF THE INVENTION

There is a need in the art to provide a systematic approach for the detection and identification of microbes which are harbored within a host organism, particularly those associated with pathogenesis. Therefore, in one aspect, the invention provides a method of using a computer system to identify a microbe inhabiting a host organism which comprises the steps of obtaining sequence information from a plurality of sequences from at least one host organism and searching a database of host organism genomic sequences to determine the presence or absence of the plurality of expressed sequences in the database. The absence of at least one of the sequences in the database indicates that the at least one sequence is a candidate microbe sequence. Individual sequences can be searched sequentially; however, preferably, sets of sequences are searched at a time.

In one aspect, the method comprises the steps of obtaining sequence information from a library of genomic DNA from a host organism and searching a database of genomic sequences from host organisms to determine the presence or absence of a sequence in the library in the database. A sequence that is present in the library but is absent in the database is identified as a candidate microbe sequence.

The microbe can be a symbiotic organism, such as a mutualistic organism, a commensal organism or a parasitic organism. The microbe can also be a pathogen. Microbes which can be identified by the method include, but are not limited to, phage, bacteria, viruses, protozoa and fungi. The host organism can be a microorganism, a plant, or an animal, such as a mammal (e.g., a human being). The host organism can also be an insect, bird, or a fish.

In one aspect, the plurality of sequences from the least one host organism comprises expressed sequences. For example, the plurality of sequences can comprise EST and/or cDNA sequences. Sequence information relating to expressed sequences can be obtained by sequencing a library of expressed sequences from one or more host organisms. Additionally, or alternatively, expressed sequence information can be obtained from a database of expressed sequences, such as an EST or cDNA database.

In one aspect, sequences from the at least one host organism suspected harboring a microbe are enriched for sequences which are present in the at least one host organism and which are not present in a plurality of host organisms which do not harbor the microbe. Enrichment can be performed using a subtractive hybridization assay, which can be a differential gene expression assay. Subtractive hybridization assays include, but are not limited to, representational difference analysis, SAGE, and suppression subtraction analysis. Alternatively, enrichment can be performed by electronically subtracting sequences from the at least one host organism which are stored in a first database from sequences of the plurality of organisms which are stored in a second database. In one aspect, the first and second databases are both expressed sequence databases and electronic subtraction is used to enrich for differentially expressed sequences which are expressed in the at least one host organism suspected of harboring a microbe and not expressed in the plurality of organisms which do not harbor the organism.

In one aspect, enriched sequences are then compared to sequences in a host organism genomic database to identify sequences in the at least one host organism suspected of harboring a microbe which are not present in the host organism genomic database. These sequences are identified as candidate sequences belonging to a microbe.

In a further aspect, one or more of the following sequences are eliminated from the host organism genomic database: vector sequences, mitochondrial sequences, repetitive sequences, sequences from other species, low quality sequences, known host organism mRNA sequences, and combinations thereof.

In a preferred aspect, the method according to the invention is used to identify the sequence of a pathogen. In this aspect, the at least one host organism is an organism which has a pathogenic condition, and sequences from the host organism (expressed or genomic) are compared to genomic sequences in a database from host organisms which do not have the pathogenic condition. The pathogenic condition can be a disease selected from the group consisting of an inflammatory disease, an autoimmune disease, and a cell proliferative disease. More particularly, the disease can be selected from the group consisting of: sarcoidosis, inflammatory bowel disease (e.g., such as Crohn's disease), atherosclerosis, multiple sclerosis, rheumatoid arthritis, type I diabetes mellitus, lupus erythematosus, Hodgkin's disease, and bronchioalveolar carcinoma. Sequences from the at least one host organism which do not match sequences in the genomic database identified as candidate sequences belonging to a pathogenic organism. In one embodiment, the pathogenic organism is an infectious disease organism.

In a further aspect, the invention provides a method of using a computer system to identify a microbe inhabiting a host organism, comprising the steps of: obtaining sequence information from a plurality of expressed sequences from at least one host organism; and searching a database of host organism genomic sequences to determine the presence or absence of the plurality of expressed sequences in the database, wherein the absence of an expressed sequence in the database identifies the expressed sequence as a candidate microbe sequence. Preferably, the plurality of sequences are from a library. Still more preferably, the library is a library of expressed sequences. In one aspect, the library comprises human sequences. In another aspect, the library comprises human sequences from one or more humans having a disease. The disease can be selected from the group consisting of an inflammatory disease, an autoimmune disease, and a cell proliferative disease. In one aspect, the disease is selected from the group consisting of sarcoidosis, inflammatory bowel disease, atherosclerosis, multiple sclerosis, rheumatoid arthritis, type I diabetes mellitus, lupus erythematosus, Hodgkin's disease, and bronchioalveolar carcinoma.

In still a further aspect, the invention provides a method of using a computer system to identify a microbe inhabiting a host organism comprising the steps of: obtaining expressed sequence information from a plurality of sequences from at least one non-microbial host organism and searching a database of microbial sequences to determine the presence or absence of the plurality of expressed sequences in the database, wherein the presence of an expressed sequence in the database identifies the expressed sequence as a candidate microbe sequence. In one aspect, the plurality of sequences are from a library of expressed sequences. In another aspect, the library of sequences comprises sequences from one or more humans having a pathological condition, e.g., such as an infectious disease.

Candidate sequences can be used as query sequences to search a database of microbial sequences, such as a database comprising bacterial and/or viral sequences. Candidate sequences also can be used to search databases comprising fungal sequences, parasitic sequences, and/or protozoan sequences. Candidate sequences also can be used as query sequences to search a non-redundant expressed sequence database comprising sequences from host organisms.

Candidate sequences or their complements can be used to probe a library of sequences from at least one microbe to identify first hybridizing sequences, preferably sequences which are longer in length (e.g., numbers of bases) than the candidate sequence. Hybridizing sequences can in turn be used to identify second hybridizing sequences which are longer in length than the first hybridizing sequences. Overlapping sequences which are identified can be used to map the genomic structure of the microbe. In some aspects, the complement of the candidate sequence is hybridized to RNA from the microbe and used to generate cDNAs.

The candidate sequence can be used to express a peptide; for example, by operably linking the candidate sequence to a promoter sequence in an expression vector. Alternatively, or additionally, sequences identified by probing a library of sequences using the candidate sequence as a probe can be used to express one or more peptides. Preferably, the peptides are antigenic. Still more preferably, the peptides can be administered to a host organism to elicit a protective immune response. Nucleic acid sequences expressing the peptides can also be administered to the host organism to elicit a protective immune response to the peptides expressed by these sequences.

The candidate sequence and/or other sequences identified by the candidate sequence can be used to detect the presence or absence of the microbe in a sample from the host organism. For example, the hybridization of the candidate sequence and/or the other sequences to nucleic acid sequences in the sample from the host organism under stringent conditions can provide an indication of the presence of the microbe in the sample. In preferred embodiments, where the microbe is a pathogen, detection of hybridization is used to provide a diagnosis that the host organism is infected by the pathogen.

Peptides expressed by the candidate sequences and/or sequences identified using the candidate sequence can be used as antigens to generate antibodies which can also be used in diagnostic assays. For example, in one embodiment, an antibody which specifically binds to a peptide expressed by the candidate sequence and/or sequences identified using the candidate sequence is contacted with a sample from the host organism and binding of the antibody to a polypeptide within the sample provides an indication that the host organism harbors the microbe.

In some embodiments, the complementary sequence of a coding sequence of the candidate sequence or of another sequence identified by the candidate sequence is administered to a host organism harboring the microbe in an amount sufficient to prevent the expression of a polypeptide encoded by the candidate sequence or the sequence identified by the candidate sequence in the host organism. The complementary sequence can further comprise a cleaving moiety for cleaving RNA (e.g., the complementary sequence can be a ribozyme).

In one aspect, a system for performing the method is provided. The system comprises a a first database comprising sequences from at least one host organism suspected of harboring a microbe and a second database comprising genomic sequences from host organisms not suspected of harboring the microbe. The system further comprises an information management system comprising a search and subtraction function for identifying sequences in the first database which are not present in the second database. In a preferred embodiment, the information management system comprises a sequence alignment function and can compare a set of sequences in the first database with all sequences in the second database. The system preferably comprises at least one user device connectable to the network and, preferably, a high speed, linear array processor.

In one aspect, the system comprises a program capable of implementing an algorithm for simultaneously comparing a plurality of sequences in a first database with all sequences in a second database, e.g., such as the algorithm implemented by the MEGABLAST program. However, in another aspect, the system comprises a program which sequentially compares a plurality of individual sequences from the first database with a plurality, and preferably all, sequences in the second database. Preferably, the system generates a result sequence set comprising sequences in the first database which do not match sequences in the genomic database.

In one aspect, the system comprises an identity or scoring matrix which requires a score of greater than or equal to 60 (e.g., equivalent to thirty identical consecutive nucleotides). In another aspect, the system iteratively computes the degree of alignment between sequences in the first and second database. Iterative computing preferably is performed using progressively smaller word sizes. In still a further aspect, the system provides one or more programs for performing one or more electronic subtraction functions for eliminating any of: vector sequences, repetitive sequences, mitochondrial sequences, sequences from non-host organisms, low quality sequences, known host organism mRNA sequences, and combinations thereof, from the genomic database.

The invention additionally provides a computer program product comprising a computer readable memory on which is embedded one or more programs for implementing any of the system functions and/or methods described above.

BRIEF DESCRIPTION OF THE DRAWINGS

The objects and features of the invention can be better understood with reference to the following detailed description and accompanying drawings.

DETAILED DESCRIPTION

Figure 1:
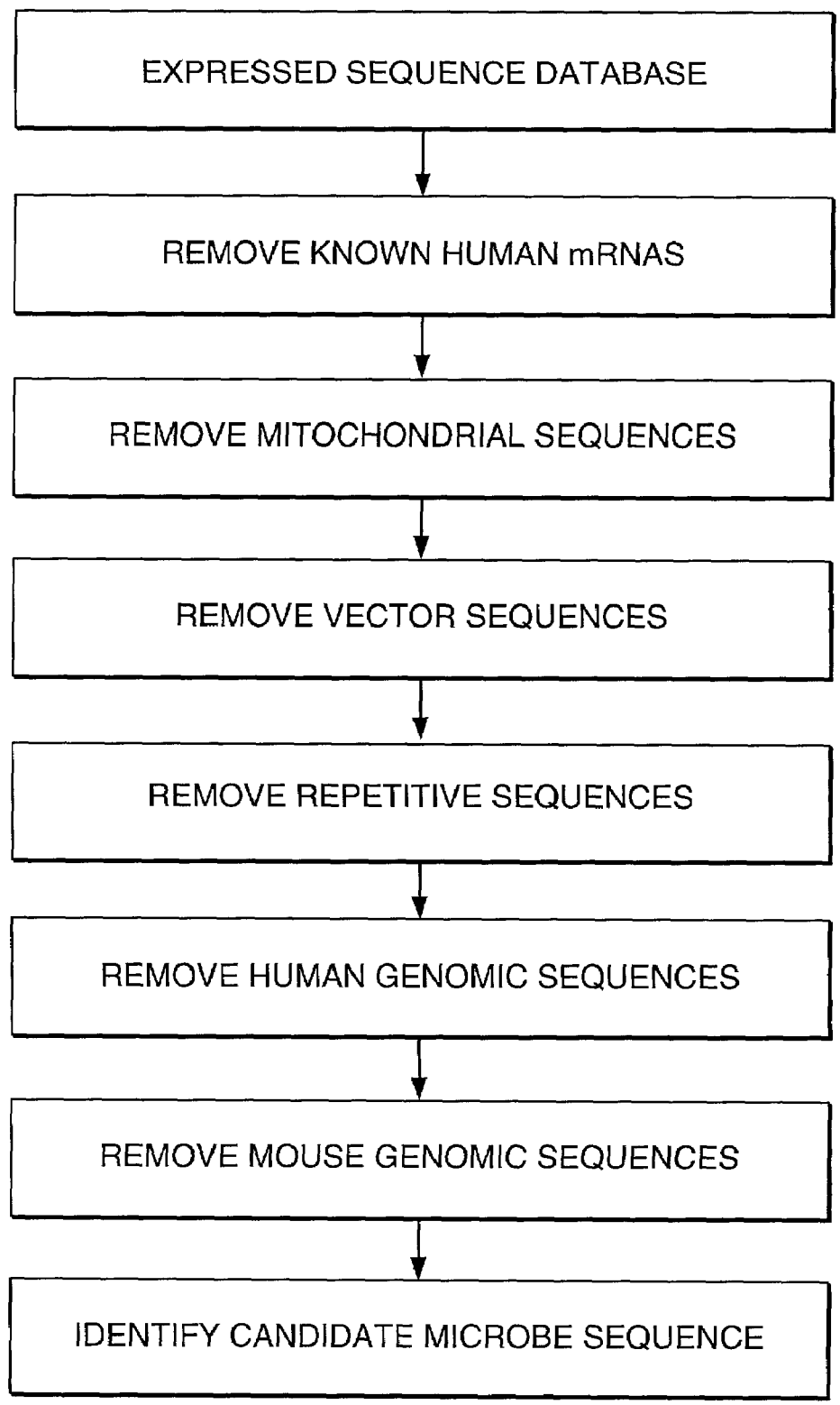
FIG. 1 is a flow chart demonstrating a method of computational subtraction analysis according to one embodiment of the invention to identify microbes harbored by a human being.

The invention provides a method and system for performing computational subtraction to detect microbes harbored by a host organism. In some aspects, the microbes are pathogens and the system is used to identify sequences belonging to these pathogens which can then be used in methods of diagnosis and treatment. Alternatively, the microbes can be symbiotic organisms, such as commensal or parasitic organisms. Preferably, candidate sequences identified as belonging to a microbe are used to isolate and clone additional sequences from the microbe.

Definitions

The following definitions are provided for specific terms which are used in the following written description.

As used herein, the term "expressed sequence" is a sequence which is transcribed. "Expressed sequence information" refers to the nucleotide sequence of an expressed sequence such as an RNA molecule, a cDNA molecule or a portion of genomic DNA which corresponds to an expressed sequence, e.g., such as those portions of a gene whose complement will become part of an RNA transcript. An expressed sequence may include both coding sequences (i.e., codons which are translated into polypeptide sequences) as well as non-coding sequence (i.e., untranslated sequences).

As used herein, "a match" between sequences refers to a level of sequence similarity equivalent to a BLAST score ranging from 40 (the equivalent of 20 consecutive identical nucleotides) to 2000 (the equivalent of 1000 consecutive identical nucleotides).

As used herein, a query sequence is "present" in a database if the database contains a sequence which matches the query sequence and is "absent" in a database if the database does not contain the matching sequence.

As used herein, a "low quality sequence" is a sequence which has greater than 2.5% N nucleotides, i.e., nucleotides whose identity cannot be determined at 95% confidence levels.

As used herein, "symbiosis" or a "symbiotic relationship" refers to an association between two organisms that live together. Symbiotic relationships include mutualistic relationships, commensalistic relationships, and parasitic relationships.

As used herein, "mutualism" or a "mutualistic relationship" refers to a mutually-beneficial association between two organisms.

As used herein, "commensalism" or a "commensalistic relationship" refers to an association between two organisms where one organism may benefit but neither is harmed.

As used herein, "parasitism" or a "parasitic relationship" refers to an association between two organisms in which one organism lives at the expense of the other organism and can cause damage to the other organism.

As used herein, a "pathogen" is an organism that can cause disease in another organism (e.g., the host organism).

As used herein, a "microbe" is any organism that can live and/or replicate within a host organism for at least a portion of its life cycle. While some microbes can exist for at least a portion of their life cycle intracellularly within the cells of a host organism, microbes which grow and/or replicate extracellularly are also encompassed within the scope of the invention. Microbes include, but are not limited to, phage, viruses, gram-positive and gram-negative bacteria, protozoa, small unicellular and multicellular eukaryotes (e.g., fungi, such as yeast), and the like. The term "microbe" and "microorganism" are used interchangeably herein.

As used herein a "host organism" can any organism that can harbor (e.g., provide a habitat and/or nutrients for) another organism. Thus, a host can be a bacteria which harbors a phage, a simple eukaryote such as yeast which can harbor a bacteria, or a mammal such as a human being which can harbor by any of the foregoing.

As used herein, "infection" refers to the growth of a pathogen in a host organism.

As used herein, an "infectious disease" refers to a disease that can be transmitted from host organism to host organism.

As used herein, a "carrier" refers to a patient who shows full recovery after infection and displaying symptoms but still carries and is capable of spreading the infectious form of a microbe.

As used herein, "a sequence identified by a candidate sequence" refers to genomic sequences of microbes to which the candidate sequence or its complement hybridizes, or to which the latter genomic sequences hybridize, under stringent conditions. In some embodiments, sequences are identified by the candidate sequence electronically, e.g., by searching a database of sequences from one or more microbes. Sequences which are identified as belonging to the same microbe as the organism from which the candidate sequence was obtained are said to be "identified by the candidate sequence."

As used herein, "stringent conditions" refer to conditions under which a sequence will specifically bind to its complement to enable detection of the complement and to distinguish the complement from other nucleic acid sequences in a sample. Stringency conditions are described in Sambrook et al., In Molecular Cloning: A Laboratory Manual, $2^{nd}$ edition, vols. 1–2, Cold Spring Harbor Press (1989), the entirety of which is incorporated by reference herein. As used herein, stringent conditions require at least 80% base pairing, more preferably, at least 90–95% base pairing, and most preferably, at least 98% base pairing.

As used herein, a "fragment" of a candidate sequence or a sequence identified by the candidate sequence refers to a sequence which is shorter in length than the candidate sequence but sufficiently long to specifically hybridize to the candidate sequence. In one embodiment, a fragment ranges in size from 6 nucleotides to one less nucleotide than the full-length sequence.

As defined herein, the "a promoter operably linked" to another sequence refers to a promoter and/or promoter element and/or enhancer element(s) capable of inducibly or constitutively causing transcription of the other sequence.

As used herein, a "bodily fluid" refers to any of blood, plasma, sera, urine, CSF fluid, sputum, breast exudates, pus, and the like.

As used herein, "computational subtraction" or "electronic subtraction" or "filtering" refers to a computational method of eliminating records (e.g., such as sequences) from a database.

Computational Subtraction

In one aspect, the invention provides a systematic method to identify sequences of microbes capable of inhabiting a host organism. The microbes can be pathogenic and associated with an infectious disease. However, the microbes can also exist symbiotically within a host organism, e.g., in a mutualistic, commensal, or parasitic relationship within the host organism. The microbe can be any of a phage, a virus (e.g., an RNA or DNA virus), a bacteria, a protozoa, or other microorganism, a small unicellular or multicellular eukaryotic organism (e.g., a fungus, such as yeast), and the like. The host organism can be a microorganism, a fungus, an animal, or a plant. Preferably, the host organism is a mammal, such as a human being or a domestic animal. However, the host organism can also be an insect, bird, or a fish. Host organism sequences can be obtained from particular tissues or cells of the host organism, or from cell lines derived from these tissues or cells, or from bodily fluids from the host organism.

The invention provides a computational subtraction method for detecting and identifying microbe sequences. The method comprises comparing the sequence information of a plurality of sequences obtained from one or more host organisms with sequences in a genomic database of host sequences to identify which of the plurality of sequences are not found (i.e., do not match other sequences) in the database. Sequences which are not found in the database are identified as candidate sequences which are likely to belong to a microbe. Preferably, sequence information from sets of sequences (two or more sequences, and preferably ten or more sequences) are compared against the entire genomic database at a time.

Any number of nucleotide sequence alignment algorithms can be used for this purpose, including those known in the art. For example, in one aspect, the algorithm of Zhang et al., J. Comput. Biol. 7(1–2): 203–14 (2000), which is embodied in one form in the MEGABLAST program, is used to compare sequences in an entire database of sequences from one or more host organisms (a "test database") against a genomic database. Smaller sets of sequences (e.g., at least two or at least ten) can also be compared. In some aspects, sequences from the plurality of sequences can be compared sequentially, individually, against genomic databases, e.g., such as by using the BLAST program described in Altschul et al., J. Mol. Biol. 215: 403–410 (1990); Madden et al., Meth. Enzymol. 266: 131–141 (1996); and Zhang et al., Genome Res. 7: 649–656 (1997), the entireties of which are incorporated by reference herein. Other programs whose goal is sequence similarity searching also can be used, such as FASTA, SSAHA, or any type of word hashing program such as is known in the art (see, e.g., Pearson, Proc. Natl. Acad. Sci. USA 85(5): 2444–2448 (1988); Leung et al., J. Mol. Biol. 221(4): 1367–1378 (1991), the which are incorporated by reference herein).

Methods of determining the significance of sequence alignments are known in the art and are described in Needleman and Wunsch, J. of Mol. Biol. 48: 444 (1970); Waterman et al., J. Mol. Biol. 147: 195–197 (1980); Karlin et al., Proc. Natl. Acad. Sci. USA 87: 2264–2268 (1990); Karlin et al., Proc. Natl. Acad. Sci. USA 90: 5873–5877 (1993); Dembo et al., Ann. Prob. 22: 2022–2039 (1994) and Altschul), In Theoretical and Computational Methods in Genome Research. (S. Suhai, ed.), pp. 1–14, Plenum, N.Y.; the entireties of which are incorporated by reference herein.

In some aspects, the genomic database is searched for short perfect matches of a set length (i.e., a word size). This enables a more rapid comparison than window/stringency matching. In one embodiment, a word size ranging from 10–30 bases is used. Preferably, a series of sequential searches is performed, using progressively smaller word sizes ranging from 30 to 10 bases. More preferably, a first search using a word search of 24 is performed, followed by a second word search of 20, followed by a third word search of 16, followed by a fourth word search of 12. In one aspect, a test sequence is shifted to the left or right of sequences in the database to identify maximal regions of alignment.

In some aspects, a scoring matrix is used to identify the likelihood that one or more sequences in the test database do not match or are absent from the genomic database. Preferably, scores of greater than or equal to 60 are required. In one aspect, the scoring matrix assigns a match if there is a BLAST score ranging from 40 (the equivalent of 20 consecutive nucleotides) through 2000 (the equivalent of 1000 consecutive nucleotides). In another aspect, a matrix is used which assigns expectation values to matches and mismatches after alignment. Expectation values can be adjusted to require that a score does not grow simply by extending the alignment in a random way. For example, in one embodiment, expectation values of from $10^{-20}$–$10^{-3}$ can be selected, and preferably, expectation values of $10^{-7}$ are used. Gap values can be set to any desired value as is routine in the art (see, e.g., Smith et al., 1981, J. Mol. Evol. 18(1): 38–46, Levitt et al., 1998, Proc. Natl. Acad. Sci. USA 95(11): 5913–5920, the entireties of which are incorporated herein by reference.

In one aspect, a results database is created, preferably comprising sequences from the test database which are ranked according to their alignment with sequences in the genomic database. Preferably, sequences which show a high degree of alignment to genomic sequences from the host organism (e.g., having at least 20–1000 consecutive identical nucleotides) are not included in the results database or are subsequently removed from the results database.

In a preferred embodiment, as shown in FIG. 1, a subtraction operation is performed to remove sequences from either the genomic database and/or the test database and/or the results database. For example, subtraction operations can be used to remove vector sequences, repetitive sequences, mitochondrial sequences, sequences from other species, low quality sequences, blown host organism mRNA sequences, and the like. It should be obvious to those of skill in the art that the order of subtraction operations is not critical and that one or more subtraction operations can be used. In certain aspects after filtering operations to filter sets of candidate sequences through one or more of a vector sequence database, a repetitive sequence database, a mitochondrial sequence database, a non-host species database, and/or a known host organism mRNA database ("filtering databases"), a first candidate sequence set of sequences is again compared to the host organism genomic database, and/or one or more filtering databases using a reduced word size than was used in the previous series of operations, to generate a second candidate sequence set which is then stored in a results database. In a preferred aspect, low quality sequences are removed, before or after filtering.

Test Database

In one aspect, the test database is an expressed sequence database of sequences from the host organism, such as an EST or cDNA database (e.g., a library database). Such databases are known in the art and include, but are not limited to, human expressed sequence databases such as the NCBI EST database, the LIFESEQ™, database (Incyte Pharmaceuticals, Palo Alto, Calif.), the random cDNA sequence database from Human Genome Sciences, the EMEST8 database (EMBL, Heidelberg, Germany), and the like (see, also, Boguski et al., 1993, Nat. Genet. 4(4): 332–333, the entirety of which is incorporated by reference herein).

Figure 2:
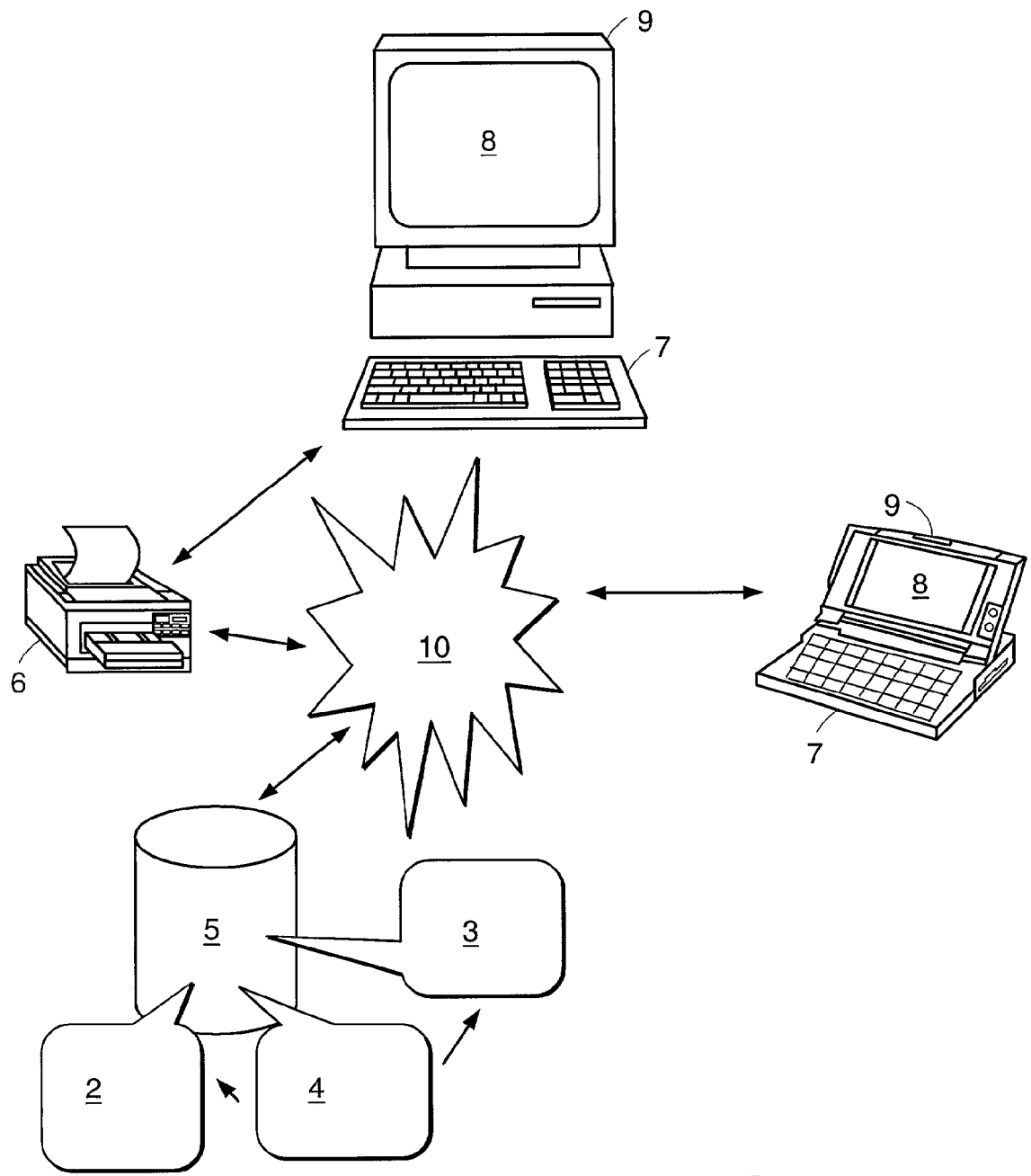
FIG. 2 is a schematic of a system according to one aspect of the invention for performing a computational subtraction analysis.

The test database also can be generated by inputting and storing sequence information obtained by sequencing a plurality of nucleic acids from a library of expressed sequences from one or more host organisms suspected of harboring a microbe, into a user device of a system 1 (shown in FIG. 2) as described further below. Libraries of expressed sequences can be generated using total RNA or polyadenylated RNA, and by using random priming or oligodT priming or a combination of these methods. Such techniques are known in the art. Libraries of particular interest include, but are not limited to, libraries of expressed sequences from one or more patients with an inflammatory disease, an autoimmune disease, and a cell proliferative disease. For example, in one aspect, libraries of expressed sequences from one or more patients with a disease selected from the group consisting of sarcoidosis, inflammatory bowel disease (such as Crohn's disease), atherosclerosis, multiple sclerosis, rheumatoid arthritis, type I diabetes mellitus, Lupus erythematosus, Hodgkin's disease, and bronchioatveolar carcinoma are used to obtain expressed sequence information. Preferably, the creation of such libraries is performed to minimize manipulation of tissue (e.g., by careful attention to sterility and avoidance of amplification methods) to avoid spurious contamination of such libraries with bacterial sequences.

While the test database can consist of entirely expressed sequences, the test database can also be a genomic sequence database. For example, the test database can comprise sequence information from a plurality of sequences in a genomic library from one or more host organisms suspected of harboring a microbe. Preferably, genomic sequence test databases are used to identify expressed sequences of microbes which are not polyadenylated (and/or which have integrated into the genome of the host organism), e.g., such as bacterial expressed sequences which would likely escape detection in expressed sequence libraries generated from polyadenylated RNA.

The test database can be enriched for sequences which are found in host organism(s) suspected of harboring a microbe and which are not found in host organisms not harboring the microbe. In one aspect, the enrichment method comprises combining genomic test sequences with other genomic sequences (reference sequences), expressed test sequences with expressed reference sequences, or expressed test sequences with genomic reference sequences, and removing sequences which are common to both test and reference sequence sets, thereby enriching for test sequences which are not found in a reference set of sequences.

For example, in one aspect, a subtractive hybridization method is used to enrich for expressed sequences in a sample of nucleic acids from a host organism which is suspected of harboring a microbe and which are not expressed in host organisms which do not harbor the microbe. Samples can comprise total nucleic acids, polyadenylated RNA, or total RNA. Subtractive hybridization methods to enrich for differentially expressed sequences are known in the art and include, but are not limited to, SAGE (Serial Amplification of Gene Expression) (see, e.g., Velculescu et al., Science 270: 484 (1995) and U.S. Pat. No. 5,866,330), subtractive hybridization of cDNA libraries (e.g., using magnetic beads, as described in WO 97/07244 A1), cDNA representational difference analysis (e.g., Hubank and Schatz, Nucl. Acids Res. 22: 5640–5648 (1994)), and suppression subtraction analysis (see, e.g., U.S. Pat. No. 5,565,340). Subtractive hybridization methods can also be used to enrich for sequences which are present at different levels in different populations of genomic DNA. Such methods include, but are not limited to, representational difference analysis, such as described in U.S. Pat. No. 5,958,738 and CLONTECH's PCR-Select™ Bacterial Genome Subtraction technique (see, e.g., Diatchenko et al., Proc. Natl. Acad. Sci. USA 93: 6025–6030 (1996); CLONTECHniques X(4): 2–5 (1995)). The entireties of these references are incorporated by reference herein.

In another aspect, enrichment is performed electronically. For example, sequences from at least one host organism suspected of harboring a microbe stored in a test database can be subtracted from sequences in a "reference database" comprising sequences from a plurality of host organisms not harboring the microbe. In one aspect, the test database and reference database are both expressed sequence databases and electronic subtraction is used to enrich for differentially expressed sequences which are expressed in the at least one host organism and which are not expressed in the plurality of host organisms. Methods for electronic subtraction analysis of expressed sequences are described in U.S. Pat. No. 6,114,114, for example, the entirety of which is incorporated by reference herein.

In some embodiments, the test database is a relational database which segregates particular types of sequences from other types of sequences within the database. For example, in one aspect, expressed sequence information can be subdivided within an expressed sequence database according to a particular tissue, or cell type, or cell line, in which the sequence is expressed. In these embodiments, particular portions of the test database can be compared to the genomic database during a search, sequentially, or simultaneously.

In one aspect, once a candidate sequence is identified, it is compared to a nucleotide sequence database comprising sequences from a plurality of species, to identify the microbial organism genus to which the sequence belongs or to which the species is related evolutionarily. For example, GenBank's nucleotide or "nt" database can be used. In another aspect, the candidate sequence can be used as a query sequence to search a database comprising only microbe sequences. In one embodiment, the database is a microbial sequence database which can be a viral sequence database, or a fungal or parasite sequence database. Such databases are known in the art and include, but are not limited to, the Incyte Microbial Database, the TIGR Microbial Database, the TIGR Parasites Database, TIGR Fungal Database, and the TIGR Viral Genome Sequencing Project Database. This step can be used to identify or evaluate the taxonomic relationship between the candidate sequence and sequences of other known microbes for which genomic sequence information is known.

In still another aspect, candidate sequences are compared to sequences in a non-redundant RNA database to determine whether the sequence matches known host organism RNA molecules. In still a further aspect, a candidate sequence is conceptually translated to identify open reading frames and the amino acid sequences of a polypeptide encoded by the candidate sequence can be used as a query sequence to search a protein sequence database comprising microbial sequences (i.e., the database can comprise multiple species sequences in addition to microbial sequences, such as the GenBank nr database, or the database can comprise exclusively microbial sequences). Preferably, the sequence is also used as a query sequence to search a nucleotide sequence database comprising microbial sequences (e.g., such as the GenBank nt database or an exclusively microbial sequence database) to identify sequence whose conceptual translations match known microbial proteins but whose nucleotide sequences do not match microbial nucleotides. These latter classes of sequences, which are preferably stored in a results database, are likely to identify sequences belonging to microbes of the same genus as the microbe whose protein was identified as a match, but which do not necessarily represent microbes belonging to the same species, i.e., the sequences are likely to represent previously uncharacterized microbes.

Genomic Databases

Genomic databases for a variety of host organisms are also known in the art, and include, but are not limited to, the NCBI GenBank database (see, e.g., http://www.ncbi.nim.nih.gov/entrez/query.fcgi?db=Genome), the Celera Human Genome (http://www.celera.com), the Genetic Information Research Institute (GIRI) (http://www.girinst.org) and Human Genome Fragment database, TIGR databases (e.g., the TIGR Human Gene Index Database), and the like.

The genomic database also can be generated by inputting and storing sequence information obtained by sequencing a plurality of nucleic acids from a genomic library of sequences from one or more host organisms which do not harbor microbes, into a user device of a system described further below.

Genomic databases contemplated according to the invention include genomic sequence information from any of the host organisms described above, e.g., from a microorganism, a fungus (e.g., yeast), an animal (insect, bird, fish, or mammal, such as a human being or domestic animal) or a plant.

System For Performing The Computational Subtraction Method

The invention further provides a system 1 for performing the computational subtraction analysis described above (see, FIG. 2). In one aspect, the system 1 comprises a first database 2 (e.g., the test database) comprising sequences from at least one host organism suspected of harboring a microbe and a second database 3 comprising genomic sequences from host organisms not harboring the microbe. The system 1 further comprises an information management system 4 comprising a search function for identifying sequences in the first database 2 which are not present in the second database 3. In a preferred embodiment, the system 1 further comprises a program embodied in a computer readable medium for executing sequence alignments between at least a first sequence in the first database and a plurality, and preferably, all sequences in the second database. The program can be part of a server 5 (which also can store program applications required by the information management system 4) or part of a processor which is part of a user device 9. Preferably, however, the user device 9 is in communication with the server 5 and/or other servers (not shown). The user device 9 can be a computer, a laptop, a wireless device, and the like. The system further can include additional user devices 9, output devices 6 (e.g., printers), and input devices (e.g., keyboards 7, mice, joysticks, and the like). The user device 9 preferably includes an interface 8 which can be displayed by the device 3 in response to the user accessing the system 1 to activate the information management system 5. The system 1 is preferably connectable to the network 10, enabling a user to access the system remotely from any user device 3 that is connectable to the network 10.

In preferred embodiments, sets of sequences (at least 2, at least 10, at least 100, or at least 500) in the test database 2 are compared at a single time with sequences in the genomic database 3. In one embodiment, the information management system 5 comprises a program which is capable of implementing an algorithm, such as the one used in the MGABLAST program for performing this function (see, e.g., Zhang et al., supra). However, in other embodiments, the at least 2, at least 10, at least 100, or at least 500 sequences are compared individually and sequentially with sequences in the genomic database 3.

In preferred embodiments, the user device 3 or the server 5 (or another host computer) comprises a high speed, linear array processor that can locate highly similar sequence segments (e.g., having a BLAST score of at least 40) from any at least two sequences. In one aspect, the processor comprises a high speed circuit chip that provides an equivalent of about 400,000 transistors or 100,000 gates, as described in U.S. Pat. No. 5,964,860, for use in performing high speed sequence analyses.

In one aspect, the system 1 further comprises an input device 7 that receives a set of sequences (either sequentially or simultaneously), a memory that stores the set of sequences (not shown), and a processor that transfers information from the set of sequences to the memory (e.g., in the form of data characters representing nucleotide bases in the set of sequences). The processor can be part of a user device 3, but is preferably part of the server 5. In another aspect, the system 1 further includes an identity matrix and a result sequence set (e.g., from the results database described above) (not shown), in which members of a set of compared sequences are ranked according to their degree of match to sequences in the genomic database 3. In a further aspect, the results sequence set can include sequences which do not match sequences in the genomic database. Sequences which have the least amount of match (as determined using parameters established by the user) can be displayed on an interface 8 of the user device 8 in response to a user query to match sequences.

In one aspect, the identity matrix is pre-selected by the user to require a match score of greater than or equal to 60 with a word size of between 10 and 30. In one embodiment, the system 1 iteratively computes the degree of alignment between sequences using progressively smaller word sizes from 30 to 10, (e.g., first using a word size of 24, then a word size of 20, then a word size of 16, then a word size of 12). Preferably, the score value remains the same and is some value greater than or equal to 60. The matrix is designed to eliminate low quality sequences (e.g., as determined using a base calling program such as PHRED), short sequences (less than 150 nucleotides), or sequences comprising a maximum number of ambiguous or unreadable nucleotides, such that there is a minimum length of quality sequences (e.g., sequences whose bases have a high confidence (at least 95%) of being accurate) of at least 50 nucleotides, and preferably at least 150 nucleotides.

In one aspect, the system 1 provide one or more programs for performing one or more electronic subtraction functions analogous to an electronic subtractive hybridization. For example, in one aspect, the system 1 is capable of eliminating, in response to a user command or in response to a pre-programmed set of instructions, any of: vector sequences, repetitive sequences, mitochondrial sequences, sequences from other species, low quality sequences, known host mRNA sequences (i.e, sequences known to belong to the host organism), and combinations thereof.

In a further aspect, the invention provides a computer program product comprising a computer readable memory on which is embedded one or more programs for implementing any of the system 1 functions described above.

Methods of Using Candidate Sequences

Cloning and Sequencing Genomic DNA From Microbes

In one aspect, candidate sequences identified using the methods and system 1 described above are used as probes to probe a library of sequences from at least one microbe. The microbe can be a phage, a virus, a bacteria, a protozoa, or other microorganism, a small unicellular or multicellular eukaryotic organism, such as a fungi (e.g., yeast), and the like. Microbes can be cultured from host organisms to provide nucleic acids suitable for generating libraries using methods known in the art. Preferably, the library is a genomic library. Alternatively, where microbes cannot be cultured, libraries can be generated from genomic or expressed sequences from which host organism sequences have been subtracted as described above. In some aspects, microbe sequences which are enriched in these samples can be ligated to linkers or adapters and amplified using primers which hybridize to these linkers or adapters. Alternatively, or additionally, the linkers or adapters can include promoter sequences and microbe sequences can be amplified by providing polymerases which recognize these sequences and the appropriate nucleotides (e.g., using a transcription-based amplification system). These methods can be complemented by additional rounds of computational subtraction as described above by sequencing enriched sequences and subtracting sequence information corresponding to these enriched sequences from a genomic database to identify enriched sequences which are not found in the genomic database.

In one aspect, candidate sequences are used to identify hybridizing sequences within the library which are longer in length than the candidate sequence, either at the 5' end or 3' end or both. These longer sequences are used, in turn, to identify other sequences which are preferably longer in length either at the 5' end or 3' end or both. Overlapping clones can be mapped using restriction enzyme analysis in combination with Southern analysis, and/or sequence analysis, to further characterize the genome structure of the microbe. Preferably, genomic sequence information is inputted into a microbial genomic database (i.e., a database comprising only microbial sequences).

Microbe sequences can be evaluated using a sequence analysis program such as the Gene Locator and Interpolated Markov Modeler, or Glimmer™, program to identify coding sequences and to distinguish such sequences from non-coding DNA (see, e.g., Salzberg et al. Nucl. Acids Res. 26(2):544–8 (1998). A version of Glimmer designed for small eukaryotes is described in Salzberg et al., Genomics 59: 24–31 (1999). The entirety of these references is incorporated by reference herein.

In one embodiment, RNA samples are obtained from host organisms harboring the microbe (e.g., total RNA or polyA RNA if the microbe's RNA is polyadenylated) and a complement of the candidate sequence is used as a primer to generate cDNA molecules from the RNAs obtained. In one embodiment, cDNAs are generated using a RACE method (see, e.g., Siebert et al., In Gene Cloning and Analysis by RT-PCR (BioTechniques Books, Natick, Mass.), pp. 305–320 (1998); Don et al., Nucl. Acids Res. 19: 4008 (1991); Roux, PCR Methods Appl. 4: 5185–5194 (1995); the entireties of which are incorporated by reference herein) to identify the 5' and or 3' end of a particular RNA transcript. Preferably, the sequences of cDNA clones are inputted into a results database for comparison to a database comprising microbial nucleotide sequences.

In some aspects, when a host organism has been identified, candidate sequences and/or their complements can be used as primers in PCR or RT-PCR assays to identify additional microbial sequences of interest, for example, in nucleic acids obtained from cultures of these microbes. In one aspect, asymmetric or one-directional PCR can be performed using the candidate sequence or its complement as a single primer in primer extension reactions to identify microbial sequences flanking the primer sequence in the microbial genome or in a microbial transcript. One-directional PCR is known in the art and is described in U.S. Pat. No. 6,184,025, for example, the entirety of which is incorporated by reference. In other aspects, at least two primers corresponding to the candidate sequence are used (e.g., primers capable of amplifying a nucleic acid fragment which comprises a subsequence of the candidate sequence of at least 50 nucleotides). In addition to detecting microbial sequences amplifiable using these primers, the primers can be used to verify that the candidate sequences do not represent previously unsequenced host genomic DNA. For example, the primers can be used in amplification reactions with host genomic DNA to verify that no amplification of host genomic sequences occurs.

Diagnostic Methods

Candidate sequences, their complements, or sequences identified by candidate sequences (e.g., such as by any of the assays described in the preceding section), can be used in hybridization assays to detect the presence of a microbe in a sample. Although such methods are described as "diagnostic", this does not imply that the method is necessarily used to determine the presence or absence of a pathogenic condition in an organism. For example, diagnostic methods can be used to detect the presence of a commensal microbe within a sample, which can, in some instances, be desirable (e.g., such as when the microbe produces vitamins for the host). In some instances, however, the hybridization assays can be used to detect the presence of one or more pathogens in a sample from an organism, and the results of such as assay can be used to provide treatment options for the organism. In still other aspects, the hybridization assays are used to detect carrier organisms which are infected by pathogens but which do not show symptoms of a pathogenic condition.

In one aspect, nucleic acids from a sample obtained from a host organism (e.g., a cell, a tissue sample, a bodily fluid, a lavage specimen, and the like) are contacted under stringent conditions with a test sequence derived from the candidate sequence. As used herein, "a test sequence derived from a candidate sequence" refers to the candidate sequence itself, or a fragment thereof, or another sequence from the microbe which the candidate sequence has been used to identify, or to complements of any of these sequences.

The test sequence can be used as a diagnostic probe to detect expressed sequences or genomic sequences of the microbes in the sample by detecting the formation of a hybridization complex between the test sequence and a nucleic acid in the sample. In one embodiment, test sequences are labeled with detectable labels. However, in other embodiments, the test sequence is bound to a molecule which is detectably labeled or which itself can bind to detectably labeled molecule(s). In one aspect, the amount of test sequences bound is used to provide an indication of the number of microbes in a sample (for example, by providing a comparison to test samples comprising a known amount of microbes). In another aspect, either the sample sequences, or probe sequences, or both, are amplified (e.g., by PCR, LCR or some other means of amplification) to increase the sensitivity of the assay. In still a further embodiment, the test sequence itself is used as a primer in an amplification assay or a reverse transcription-based assay. Methods of labeling, hybridizing, amplifying and quantitating nucleic acids are known in the art. Probes can be obtained by restriction digestion of cloned sequences or can be synthesized using means known in the art. PNA probes can also be used to enhance the specificity of assays.

In some embodiments, panels of nucleic acid sequences representing different regions of the genome of the microbe can be used simultaneously or sequentially to detect the microbe. In still another embodiment, panels of nucleic acid probes from different microbes can be used in the diagnostic assays described above. The probes, or oligonucleotides comprising probe sequences, can be immobilized on a substrate (e.g., a microarray) as described in Cummings et al., supra, to increase the throughput of diagnostic assays.

In one aspect, the candidate sequence, or a sequence identified by the candidate sequence, is used to express a peptide, for example, by operably linking the candidate sequence to a promoter sequence in an expression vector. In some embodiments, the candidate sequence is linked in frame to a cleavable amino acid sequence whose expression is operably linked to the promoter sequence. Alternatively, a peptide can be synthesized using the predicted amino acid sequence of the candidate sequence or a coding sequence of the sequence identified by the candidate sequence. Preferably, the peptide is an antigenic peptide. The peptide can be used to generate antibodies which specifically bind to the peptide and to polypeptides or proteins comprising the peptide.

Methods of generating antibodies are know in the art and are described in Kohler and Milstein, Nature 256: 495–497 (1975); Kosbor et al., Immunology Today 4: 72 (1983); Cote et al., Proc. Natl. Acad. Sci. U.S.A. 80: 2026–2030 (1983), (Morrison et al., Proc. Natl. Acad. Sci. U.S.A. 81: 6851–6855 (1985); Neuberger et al., Nature 312: 604–608 (1984); Takeda et al., Nature 314: 452–454 (1985); and U.S. Pat. No. 4,946,778, the entireties of which are incorporated by reference herein. Antibodies encompassed within the scope of the invention include, but are not limited to, monoclonal antibodies, polyclonal antibodies, double chain antibodies, single chain antibodies, chimeric antibodies, antibody fragments comprising at least one antigen binding site, and the like.

In one aspect, antibodies specific for peptides expressed by nucleic acids from the microbe are used in histological assays, such as immunohistochemistry, immunofluorescence, immunoelectron microscopy, and the like. However, antibodies can also be used in immunoassays as are routine in the art. The detection of binding of an antibody to a sample from a host organism suspected of harboring a microbe can be used to provide a diagnosis that the organism harbors the microbe (e.g., that the microbe may be found on or within its cells, or in bodily fluids from the organism). For example, the antibodies according to the invention can be used to detect microbes which are shed by host cells and which may be present in bodily fluids outside of cells or in proximity to cells or tissues from the host organism, or to detect antigens which are presented after processing of polypeptides of a microbe by host cells (e.g., by host cell MHC class I molecules), or to detect microbes which typically exist extracellularly within a host organism, such as bacteria.

As with the nucleic acid probes described above, panels of antibodies specific for a single microbe can be used as probes, either simultaneously or sequentially. Panels of antibodies specific for a plurality of microbes can also be used. In one embodiment, antibodies are arrayed on a substrate to increase the throughput of the analysis.

In some aspects, peptides themselves can be used as diagnostic reagents. For example, peptides can be reacted from sera from an organism suspected of containing a microbe to detect the presence of circulating antibodies which react with the peptides.

Antisense Nucleic Acid Molecules

In one aspect, the invention provides a sequence which is a complement or an antisense sequence of a coding sequence of the candidate sequence or of the coding sequence of another sequence which has been identified by the candidate sequence. The antisense sequence can be administered to a host organism in an amount sufficient to prevent the expression of a polypeptide encoded by the candidate sequence or the other sequence identified by the candidate sequence. Techniques of generating antisense constructs are known in the art and are described in, for example, Stein et al., Cancer Research 48: 2659–2668 (1988); Walder, Genes & Development 2: 502–504 (1988); Marcus-Sekura, Anal. Biochemistry 172: 289–295 (1988); Zon, J. of Protein Chemistry 6: 131–145 (1987); Zon, Pharmaceutical Research 5: 539–549 (1988); and Loose-Mitchell, TIPS 9: 45–47 (1988); the entireties of which are incorporated by reference. Antisense nucleic acids according to the invention additionally can be modified to enhance their stability in vivo, as described in Agrarwal et al., Proc. Natl. Acad. Sci. USA 85: 7079 (1988), and Sarin et al., Proc. Natl. Acad. Sci. USA 85: 7448 (1988), for example, the entireties of which are incorporated herein by reference.

Antisense nucleic acids also can be modified to include a cleaving agent for cleaving a molecule to which the antisense nucleic acid binds. For example, the nucleic acid can be engineered to sequences which provide the function of a ribozyme. Sequences for use in constructing ribozyme vectors are described in, for example, Rossi et al., Aids Research and Human Retroviruses 8: 183 (1992); Hampel and Tritz, Biochemistry 28: 4929 (1989); Hampel et al., Nucleic Acids Research 18: 299 (1990); Perrotta et al., Biochemistry 31: 16 (1992); Guerrier-Takada et al., Cell 35: 849, (1983); U.S. Pat. No. 4,987,071; Scanlon et al., PNAS 88: 10591–5 (1991), Dropulic et al., J Virol. 66: 1432–41 (1992); Weerasinghe et al., J Virol. 65: 5531–5534 (1991); Ojwang et al., PNAS 89: 10802–10806 (1992); Chen et al., Nucleic Acids Res. 20: 4581–1589 (1992); and Sarver et al., Science 247: 1222–1225 (1992); the entireties of which are incorporated herein by reference.

Antisense molecules can be administered directly to a target site. For example, antisense molecules can be administered topically (e.g., to skin), by direct injection into cells (e.g., such as tumor cells), by direct administration to a tissue which has been exposed by surgery, or through a medical access device, such as a catheter or endoscope, which can deliver the molecule directly to the target site (e.g., by bringing the tissue into contact with a solution comprising the antisense molecules). In another aspect, antisense molecules are administered to the patient enterally or parenterally. Antisense molecules can be administered with suitable carrier molecules to facilitate delivery to a target site (e.g., by complexing the molecules with liposomes) and/or can be bound to a targeting molecule (e.g., a ligand specific for a receptor expressed on the surface of a host cell infected by the microbe). Preferably, the targeting molecule includes an intracellular localization signal for delivering the antisense molecule to the interior of the cell.

Therapeutic Peptides

As discussed above, candidate sequences, or sequences identified by these sequences, can be used to generate peptides. In some aspects, the peptides are administered to the host organism in an amount sufficient to enable the host organism to mount a protective immune response against the microbe. In a preferred embodiment, the peptides are used as a vaccine. Alternatively, or additionally, nucleic acid sequences which encode these peptides and which are operably linked to one or more promoter elements can be administered to the host organism in an amount sufficient to enable the host organism to mount a protective immune response against the microbe (e.g., providing a DNA vaccine). A protective immune response can include the production of macrophages which specifically recognize the microbe (e.g., during an extracellular portion of its life cycle) and/or the production of cells which produce neutralizing antibodies which specifically bind to the microbe and which prevent the microbe from infecting further cells.

In some aspects, a plurality of peptides from the same microbe or a nucleic acid expressing the plurality of peptides is administered to the organism. In some embodiments, the microbe is isolated and nucleic acids removed, and the microbe itself is administered to an organism to generate a protective immune response (see, e.g., as described in U.S. Pat. No. 5,698,430, the entirety of which is incorporated by reference herein).

EXAMPLES

The invention will now be further illustrated with reference to the following examples. It will be appreciated that what follows is by way of example only and that modifications to detail may be made while still falling within the scope of the invention.

Example 1

Computational subtraction was used to identify sequences in an EST library (Unigene library #271) from the HeLa cervical carcinoma cell line. This library contains 7,073 EST's. 6,752 of these EST's comprise at least 100 discrete, unambiguous 15-mers (e.g., sequences whose nucleotide identity can be assigned at greater than 95% confidence levels or 0% N's). A system 1 according to the invention was used to compare the sequences in the EST library against known human mRNA sequences, human repeat sequences, human mitochondrial sequences, the Human Genome Project (HGP) and Celera Genomics Human Genomic DNA sequences and to eliminate matching sequences. Matches within mouse genomic DNA sequences (Celera) were also searched for and removed under the assumption that these would represent unsequenced regions of the human genome.

Using a BLAST score cut-off of 60, equivalent to 30 consecutive identical nucleotides, and an expectation value of $10^{-7}$ as a cutoff, the 7,073 EST's were pared down to 144 non-matching sequences. Application of a quality filter to set a minimum length cut-off of 150 nucleotides and a 2.5% maximum ratio of ambiguous nucleotides (e.g., >2.5% N's) to non-ambiguous nucleotides, decreased the number of matching sequences to 43. When the 43 remaining sequences were matched to the GenBank nt database, 17 sequences matched additional human mRNA sequences and 6 matched known E. coli sequences.

Thus, using the system 1, 7,073 EST's in HeLa cells were reduced to a total of 22 sequences that failed to match human, mouse, or E. coli genomic sequences. Two of these sequences were subsequently determined to be identical to human papillomavirus (HPV) type 18 sequences. HPV is a cause of cervical cancer and HPV nucleic acids are known to be present in the HeLa cell line (see, e.g., Boshart et al., 1984, EMBO 3(5): 1151–1157). Two other HPV sequences were present in the HeLa cell EST library, but were filtered out by the system 1 because of a match to sequences in the Celera genome database. These two sequences match a HPV type 45 sequence from the NCBI database that was included in the Celera genome assembly but not in the NCBI assembly, thus, verifying the ability of the system 1 to identify microbial sequences through computational subtraction.

To determine which of the unmatched sequences (i.e., candidate sequences) represented unsequenced human genomic DNA and to determine whether candidate sequences could be used to identify pathogenic DNA (e.g., such as HPV DNA), PCR primers corresponding to each of the 22 non-matching sequences were generated and tested on a panel of normal human genomic DNA samples and Hela cell genomic DNA. Ten primer sequences were capable of amplifying nucleic acids in all samples of human genomic DNA, while ten primer sequences could not amplify any samples, and two primers (corresponding to HPV sequences) were able to amplify only HeLa cell genomic DNA. The ten sequences which amplified all human genomic DNA samples are likely to represent previously unsequenced regions of the human genome, while those primer sequences unable to amplify sequences in any samples are likely to represent sequences brought together by splicing (and which are therefore too far apart in genomic DNA to be amplified), sequences of non-human origin, or sequencing errors.

These results demonstrate that the system 1 is capable of identifying microbial sequences (e.g., such as HPV sequences) by computational subtraction.

Example 2

Given the ability of computational subtraction to detect viral sequences in HeLa cells, computational subtraction was used to scan existing EST databases for candidate microbial sequences using the same method as described in example 1. EST's in a NCBI EST database of 3,287,578 sequences were serially compared against filter databases using the MEGABLAST tool with a word-size of 24, to filter or subtract matching sequences. The sequences were filtered through a known human mRNA database (the NCBI RefSeq human mRNA database), which after subtraction left 1,438,967 sequences, a human mitochondria database, which after subtraction left 1,409,118 sequences, a vector sequence database (the NCBI UniVec database), which after subtraction left 1,396,697 sequences, a human repetitive sequence database (GIRST HumRep), which after subtraction left 1,368,895 sequences, a human genome database, which after subtraction left 144,498 sequences, and a mouse genome database, which after subtraction left 137,011 sequences. To improve the sensitivity of the filtering process, remaining EST's were re-run against the filters at a lower word size (20) and matching EST's were again removed, leaving 120,792 EST's unmatched. The process was repeated using a word size of 16, leaving 102,009 EST's unmatched. This last sequence set was passed through a quality filter as described in Example 1, to remove short (<150 nucleotides) and ambiguous (>2.5% N's) sequences. At the end of this subtraction or filtering process, 65,839 sequences of 3,287,578 EST sequences or 2% of the EST sequences in the NCBI EST database were found not to match a panel of human genomic or reference sequences.

Sequences were subsequently tested by BLASTN searches against GenBank nt databases (i.e., a database comprising multiple species' sequences, including microbial sequences) using (using a word size of 16) and by BLASTX searches against the nr non-redundant protein databases (using a word size of 3). A results database of these matches is available at http://www.hcs.harvard.edu/~weber/meyerson2/ nrnt.cgi, the entirety of which is incorporated by reference herein.

Despite filtering sequences against human genomic and other databases (e.g., removing matching sequences), a significant fraction of the remaining EST's still matched nucleotide and/or protein sequences of known human origin. In total, 5,119 "non-matching" candidate sequences matched nucleotide sequences from Homo sapiens using a BLASTN score minimum of 100, while the translations of 211 sequences, without nucleotide matches, matched Homo sapiens protein sequences, with a BLASTX minimum score of 100. These data are consistent with the as-yet incomplete sequencing of the human genome.

Strikingly, a significant number of sequences with matches to viral, fungal, bacterial, and plant sequences were found in the non-matching, i.e., candidate sequence set. A culled set of matching species sequences was generated by excluding all vertebrate, as well as Escherichia, Saccharomyces, Drosophila, and Caenorhabditis sequences that might represent library contamination. Using BLASTN and BLASTX minimum scores of 100, 1,055 sequences were found which matched nucleotide sequences from the culled species (i.e., sequences representing likely contaminants) and 759 sequences were found which matched culled protein sequences but not nucleotide sequences. Matches to microbial sequences are described in Tables 1 through 3.

TABLE 1

Viral Genomes With Nucleotide Similarity to Filtered Human EST Sequences

| Viral Species | EST Count | Library Count* | Tissue Types | Library No.*** |
|---|---|---|---|---|
| Hepatitis B virus | 33 | 2 | adult liver, hepatocellular carcinoma | 3618 (adult liver) |
| Human spumaretrovirus | 10 | 1 | fetal liver | 168 (fetal liver) |
| Cytomegalovirus | 9 | 3 | nervous system, breast, uterus | 2915 (nervous system) |
| Human adenovirus 2 | 8 | 6 | lymph, ovary (2)**, colon, head and neck, lung | 2222 (lymph) |
| Simian sarcoma virus | 7 | 6 | breast | 3633 (breast) |
| Human papillomavirus (subtypes 16 and 18) | 7 | 3 | cervix, placenta, uterus, tumor | 271 (cervical carcinoma cell line, i.e., HeLa) |
| Stealth virus 1 | 4 | 2 | head and neck (2) | 4582 (head and neck) |
| Kaposi's sarcoma associated virus (HHV-8) | 3 | 2 | nervous, head & neck | 2836 (nervous system) |
| Hepatitis C virus | 2 | 1 | bone marrow | 4862 (bone marrow) |

TABLE 1-continued

Viral Genomes With Nucleotide Similarity to Filtered Human EST Sequences

| Viral Species | EST Count | Library Count* | Tissue Types | Library No.*** |
|---|---|---|---|---|
| Epstein-Barr virus (HHV-4) | 1 | 1 | lymph | 5167 (lymph) |

*"Library Count" reflects the number of libraries in which EST matches to a particular virus were found.
**The total number of different libraries of a given tissue type is indicated in parentheses (if greater than one).
***Library numbers are based on UniGene assignments.

EST sequences that passed all filters (e.g., remained present after computational subtraction against one or more databases) were compared to GenBank's nt database (a database representing multiple species) using the MEGA-BLAST algorithm. Alignments with a bit score of 100 or greater were categorized as "matching" those in the nt database. Sequences remaining after subtraction which match viral genome sequences are shown in Table 1. Included in these sequences were sequences belonging to a variety of pathogenic viruses. As shown in Table 1, the most common viral match was to Hepatitis B virus sequences, for which there were 33 EST matches in the databases. Thirty-two of these matches were derived from the library GKC which is made from normal liver tissue from a Chinese patient with hepatocellular carcinoma. Hepatitis B virus sequences are abundant in this library, representing 0.2% of the 16,743 total sequences in this library. As seen in Table 1, a variety of other pathogenic virus sequences including human papillomavirus; adenovirus; and a variety of herpesviruses, including cytomegalovirus, Epstein-Barr virus, and Kaposi's sarcoma herpesvirus; were identified by computational subtraction methods according to the invention.

Table 2, below, summarizes sequences remaining after computational subtraction which match bacterial sequences. After identifying expressed sequences as candidate sequences not found in the human genome, these sequences were compared to the GenBank nt database using the BLASTX algorithm (BLAST 2.0) and alignments with a bit score of 100 or greater where catagorized as matches. Table 2 shows the ten most frequently appearing bacterial sequences after computational subtraction. As can be seen from Table 2, there are numerous matches to *Pseudomonas aeruginosa* sequences, a common pathogen as well as a commensal organism. In addition, there are numerous matches to other Pseudomonas species.

TABLE 2

Bacterial Genomes With Nucleotide Similarity To Filtered Human EST Sequences

| Bacterial species | EST Count | Library Count* | Tissue Types | Most Common Library No.*** |
|---|---|---|---|---|
| Pseudomonas aeruginosa | 304 | 85 | breast (21)**, head and neck (11), bone marrow (8) | 3025 (bone marrow) |
| Xylella fastidiosa | 92 | 32 | head and neck (12), breast (10), stomach (3) | 1304 (breast) |
| Pseudomonas sp. | 56 | 11 | breast (3), lymph 92), B-cells, muscle, ovary | 4873 (uterus) |
| Pseudomonas putida | 32 | 17 | head and neck (6), breast (5), bone marrow (2) | 1148 (breast) |
| Caulobacter cresentus | 29 | 7 | thymus (2), colon, lymph, uterus | 3587 (thymus) |
| Mesorhizobium loti | 26 | 13 | lymph (2), thymus (2), foreskin, breast | 2223 (lymph) |
| Fusobacterium naviforme | 17 | 5 | head and neck (4), uterus | 4796 (head and neck) |
| Leptotrichia-like sp. | 17 | 10 | uterus (9), head and neck (1) | 4796 (uterus) |

*"Library Count" reflects the number of libraries in which EST matches to a particular bacteria were found.
**The total number of different libraries of a given tissue type is indicated in parentheses (if greater than one).
***Library numbers are based on UniGene assignments.

The more interesting category of bacterial matches is shown in Table 3 which shows the set of bacterial sequences whose conceptual translations match known bacterial proteins and which do not share significant nucleotide sequence similarity with known bacterial nucleotide sequences. These sequences were identified by passing EST sequences through the filter databases described above and comparing remaining sequences to the GenBank nt database using the BLASTN algorithm (with a threshold of 60 bits) and to the non-redundant ("nr") protein database using the BLASTX algorithm (setting a threshold of 100 bits). EST's matching the nr database but not the nt database were categorized as "translation-only alignments." These series of operations revealed numerous pathogens with matches only to translated sequences. Again, many matches were found to *Pseudomonas aeruginosa* sequences. Other candidate sequences included those whose translated sequences matched proteins of *Mycobacterium tuberculosis*, *Vibrio cholerae* and *Neisseria meningitidis*. This suggests the presence of clones representing novel unsequenced bacteria, highly related to these pathogens, but previously undescribed, in the libraries.

TABLE 3

Sequences in Human EST Libraries With Translation Matches to Bacterial Sequences

| Bacterial Species* | EST count | Library Count** | Most Common Tissue Types | Most Common Library No.**** |
|---|---|---|---|---|
| *Pseudomonas aeruginosa* | 239 | 96 | breast (20)***, head and neck (14), bone marrow (8), CNS (7) | 3587 (thymus) |
| *Caulobacter crescentus* | 32 | 17 | thymus (3), breast (3), lymph (3) | 2223 (lymph) |
| *Xylella fastidiosa* | 22 | 14 | lymph (3), thymus (2), lung (2) | 3587 (thymus) |
| *Mycobacterium tuberculosis* | 14 | 8 | thymus (2) | 2223 (lymph) |
| *Streptomyces coelicolor* | 29 | 14 | thymus (2), breast (2), lymph (2) | 2223 (lymph) |
| *Vibrio cholerae* | 13 | 11 | ovary (2) | 2217 (B cells) |
| *Bacillus subtilus* | 14 | 10 | heart (2) | 47 (heart) |
| *Neisseria meningitidis* | 12 | 10 | thymus (3), breast (2) | 650 (pooled) |
| *Pseudomonas putida* | 11 | 4 | bone marrow (2), lymph (1), thymus (1) | 3587 (thymus) |

*Bacterial species to which candidate sequences are related, as determined by matching conceptual protein translations of candidtae sequences but not matching nucleotide sequences of candidate sequences.
**"Library Count" reflects the number of libraries in which EST matches to a particular bacteria were found.
***The total number of different libraries of a given tissue type is indicated in parentheses (if greater than one).
****Library numbers are based on UniGene assignments.

In each of the Examples discussed above, sequence analysis was performed using sequence available from the NCBI (http://ncbi.nlm.nih.gov.), Celera Genomics (http://www.celera.com) and the Genetic Information Research Institute (GIRI) (http://www.girinst.org). Human EST sequences and library information, Human Genome Project Sequences (phases 0–3), the RefSeq human mRNA set, and UniVec vector sequences were downloaded from NCBI on Mar. 6, 2001. The "nr" and "nt" BLAST databases were downloaded from NCBI on Mar. 30, 2001. The human mitochondrial genome sequence is GenBank accession # NC_001807. The HeLa cell EST library analyzed is available as Library 271 (Stratagene_HeLa_cell_s3_937216) in the UniGene resource at the NCBI web-site. The Celera draft of the human genome and the 3× coverage of shotgun sequence from the mouse genome were downloaded from Celera's website in January, 2001. RepBase6.2 was downloaded from the GIRl database on Mar. 7, 2001.

Variations, modifications, and other implementations of what is described herein will occur to those of ordinary skill in the art without departing from the spirit and scope of the invention.

What is claimed is:

1. A method of using a computer system to evaluate nucleic acid sequences of a non-microbial host organism for the presence of a candidate microbial sequence indicative of the presence of a microbe in a host organism, comprising the steps of:
   a) obtaining sequence information from a plurality of sequences from a host organism; and
   b) searching a database of host organism genomic sequences to determine the presence or absence of said plurality of sequences in said database, wherein a sequence is present in said database if it contains 20 consecutive nucleotides of sequence identical to a sequence in said database, wherein the absence of at least one of said sequences in said database indicates that said at least one sequence is a candidate microbial sequence wherein the absence of said candidate microbial sequence in said database is indicative of the presence of a microbe in said host organism.

2. A method of using a computer system to evaluate nucleic acid sequences of a non-microbial host organism for the presence of a candidate microbial sequence indicative of the presence of a microbe in a host organism, comprising the steps of:
   a) obtaining sequence information from a library of genomic DNA from a host organism suspected of harboring a microbe; and
   b) searching a database of host organism genomic sequences from host organisms to determine the presence or absence of a sequence in said library in said database, wherein a sequence is present in said database if it contains 20 consecutive nucleotides of sequence identical to a sequence in said database;
   wherein the absence of said sequence indicates that said sequence is a candidate microbe sequence, which is indicative of the presence of a microbe in said host organism.

3. A method of using a computer system to evaluate nucleic acid sequences of a non-microbial host organism for the presence of a candidate microbial sequence indicative of the presence of a microbe in a host organism, comprising the steps of:
   a) obtaining sequence information from a plurality of expressed sequences from a host organism; and
   b) searching a database of host organism genomic sequences to determine the presence or absence of said plurality of expressed sequences in said database, wherein a sequence is present in said database if it contains 20 consecutive nucleotides of sequence identical to a sequence in said database andwherein the absence of at least one of said expressed sequences in said database indicates that said at least one sequence is a candidate sequence belonging to a microbe, which is indicative of the presence of a microbe in said host organism.

4. The method according to claim 1, 2, or 3, further comprising the step of comparing said candidate sequence to a database of microbial sequences, wherein the presence of a said candidate sequence in said database of microbial sequences identifies said candidate sequence as belonging to a microbial organism.

5. The method according to claim 4, wherein said database of microbial sequences comprises sequences belonging to a symbiotic, mutualistic, commensal, parasitic or pathogenic microbial organism.

6. The method according to claim 4, wherein said database of microbial sequences includes viral sequences.

7. The method according to claim 1, 2, or 3, further comprising the step of comparing said candidate sequence to a database of microbial sequences, wherein said database comprises sequences from a pathogenic organism, wherein the presence of a said candidate sequence in said database of microbial sequences identifies said candidate sequence as belonging to a pathogenic organism.

8. The method according to claim 7, wherein said pathogenic organism is an infectious disease organism.

9. The method according to claim 7, wherein said pathogenic organism is associated with a pathogenic condition selected from the group consisting of an inflammatory disease, an autoimmune disease, and a cell proliferative disease.

10. The method according to claim 9, wherein said disease is selected from the group consisting of sarcoidosis, inflammatory bowel disease, atherosclerosis, multiple sclerosis, rheumatoid arthritis, type I diabetes mellitus, lupus erythematosus, Hodgkin's disease, and bronchioalveolar carcinoma.

11. The method according to claim 3, wherein said expressed sequences are EST sequences.

12. The method according to claim 11, wherein said candidate sequence is identified by comparing sequences in a database of expressed sequences with said sequences in said genomic database.

13. The method according to claim 3, wherein said expressed sequences are cDNA sequences.

14. The method according to claim 1, 2, or 3, wherein said host organism is an animal.

15. The method according to claim 14, wherein said animal is a mammal.

16. The method according to claim 15, wherein said mammal is a human.

17. The method according to claim 14, wherein said animal is an insect, bird, or a fish.

18. The method according to claim 3, wherein said expressed sequences are identified using a differential gene expression assay.

19. The method according to claim 18, wherein said differential gene expression assay is selected from the group consisting of SAGE, cDNA representational difference analysis, and suppression subtraction analysis.

20. The method according to claim 3, wherein said sequence information from a plurality of expressed sequences comprises sequences identified using a subtractive hybridization method.

21. The method according to claim 20, wherein said subtractive hybridization method is representational difference analysis.

22. The method according claim 1, 2 or 3, wherein said plurality of sequences are compared to said database of host genomic sequences simultaneously.

23. The method of claim 1, 2, or 3 wherein said host organism in step (a) has a pathogenic condition.

24. The method according to claim 23, wherein said plurality of sequences are compared simultaneously with sequences in said database of host genomic sequences.

25. The method according to claim 23, wherein said pathogenic condition is an infectious disease.

26. The method according to claim 23, wherein said pathogenic condition is selected from the group consisting of an inflammatory disease, an autoimmune disease, and a cell proliferative disease.

27. The method according to claim 26, wherein said pathogenic condition is selected from the group consisting of sarcoidosis, inflammatory bowel disease, atherosclerosis, multiple sclerosis, rheumatoid arthritis, type I diabetes mellitus, lupus erythematosus, Hodgkin's disease, and bronchioalveolar carcinoma.

28. The method according to claim 1, 2 or 3, wherein said host organism is a microorganism, a fungus, or a plant.

29. The method according to claim 1, 2, or 3, wherein any of: vector sequences, repetitive sequences, mitochondrial sequences, non-host species sequences, known host organism sequences, and combinations thereof are eliminated from the genomic database comprising sequences from the host organism.

30. The method according to claim 1, 2 or 3, wherein said searching is performed iteratively using progressively smaller word sizes.

31. A method of using a computer system to evaluate nucleic acid sequences of a non-microbial host organism for the presence of a candidate microbial sequence indicative of the presence of a microbe in a host organism, comprising the steps of:

obtaining sequence information from a plurality of expressed sequences from a human host organism; and searching a database of host organism genomic sequences to determine the presence or absence of the plurality of expressed sequences in the database, wherein a sequence is present in said database if it contains 20 consecutive nucleotides of sequence identical to a sequence in said database, wherein the absence of an expressed sequence in the database identifies the expressed sequence as a candidate microbial sequence, wherein the absence of said candidate microbial sequence in said database is indicative of the presence of a microbe in said host organism.

32. The method according to claim 31, wherein said plurality of sequences are from a library of sequences.

33. The method according to claim 32, wherein said library comprises human sequences from one or more humans having a pathological condition.

34. The method according to claim 33, wherein said pathological condition is a disease selected from the group consisting of an inflammatory disease, an autoimmune disease, and a cell proliferative disease.

35. The method according to claim 34, wherein said disease is selected from the group consisting of sarcoidosis, inflammatory bowel disease, atherosclerosis, multiple sclerosis, rheumatoid arthritis, type I diabetes mellitus, lupus erythematosus, Hodgkin's disease, and bronchioalveolar carcinoma.

36. The method according to claim 31, wherein said step of obtaining sequence information comprises sequencing expressed sequences cloned in a library of expressed sequences.

* * * * *